(12) United States Patent
Harding et al.

(10) Patent No.: US 8,366,676 B2
(45) Date of Patent: Feb. 5, 2013

(54) VASCULAR ACCESS DEVICE GAS DISPLACEMENT

(75) Inventors: Weston F. Harding, Lehi, UT (US); S. Ray Isaacson, Roy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 631 days.

(21) Appl. No.: 11/931,597

(22) Filed: Oct. 31, 2007

(65) Prior Publication Data

US 2008/0108973 A1 May 8, 2008

Related U.S. Application Data

(60) Provisional application No. 60/864,113, filed on Nov. 2, 2006.

(51) Int. Cl.
*A61M 5/315* (2006.01)
*A61M 5/178* (2006.01)
*F16K 1/00* (2006.01)

(52) U.S. Cl. .......... 604/167.04; 604/236; 251/334; 128/912

(58) Field of Classification Search ........ 604/167.01, 604/167.02, 167.03, 201, 203, 236, 237, 604/244, 245, 249, 256, 283, 411, 415, 533, 604/905; 251/118, 149.1, 149.6, 334; 128/912
See application file for complete search history.

(56) References Cited

U.S. PATENT DOCUMENTS

| | | | |
|---|---|---|---|
| 4,765,588 A | 8/1988 | Atkinson | |
| 4,935,010 A * | 6/1990 | Cox et al. ............ | 604/122 |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |
| 5,820,601 A | 10/1998 | Mayer | |
| 5,957,898 A | 9/1999 | Jepson et al. | |
| 6,050,978 A * | 4/2000 | Orr et al. ............ | 604/249 |
| 6,068,011 A * | 5/2000 | Paradis ............ | 137/1 |
| 6,171,287 B1 | 1/2001 | Lynn et al. | |
| 6,261,282 B1 | 7/2001 | Jepson et al. | |
| 6,344,033 B1 | 2/2002 | Jepson et al. | |
| 6,595,964 B2 | 7/2003 | Finley et al. | |
| 6,651,956 B2 | 11/2003 | Miller | |
| 6,669,681 B2 | 12/2003 | Jepson et al. | |
| 6,695,817 B1 | 2/2004 | Fangrow, Jr. | |
| 6,840,501 B2 | 1/2005 | Doyle | |
| 6,866,656 B2 | 3/2005 | Tingey et al. | |
| 6,908,459 B2 * | 6/2005 | Harding et al. ............ | 604/533 |
| 6,916,309 B2 | 7/2005 | Fangrow, Jr. | |
| 7,014,169 B2 * | 3/2006 | Newton et al. ............ | 251/149.6 |
| 7,033,339 B1 | 4/2006 | Lynn | |
| 7,104,520 B2 | 9/2006 | Leinsing et al. | |
| 7,184,825 B2 | 2/2007 | Leinsing et al. | |
| 7,244,249 B2 | 7/2007 | Leinsing et al. | |
| 2002/0193752 A1 | 12/2002 | Lynn | |
| 2003/0050610 A1 | 3/2003 | Newton et al. | |

(Continued)

*Primary Examiner* — Kevin C Sirmons
*Assistant Examiner* — William Carpenter
(74) *Attorney, Agent, or Firm* — Jeanne Lukasavage; Craig Metcalf; Kirton McConkie (57) ABSTRACT

A vascular access device may include a gas chamber housed between a body and a septum, and a receptacle in communication with the gas chamber. A method of displacing gas in a medical device may include transferring gas between a gas chamber of a vascular access device and a receptacle housed within the vascular access device.

11 Claims, 7 Drawing Sheets

U.S. PATENT DOCUMENTS

| | | |
|---|---|---|
| 2003/0120221 A1 | 6/2003 | Vaillancourt |
| 2004/0073171 A1* | 4/2004 | Rogers et al. ............ 604/164.13 |
| 2004/0124388 A1 | 7/2004 | Kiehne |
| 2004/0199126 A1 | 10/2004 | Harding et al. |
| 2004/0206924 A1 | 10/2004 | Newton et al. |
| 2005/0256500 A1 | 11/2005 | Fujii |
| 2007/0225635 A1* | 9/2007 | Lynn ............................... 604/30 |

* cited by examiner

VASCULAR ACCESS DEVICE GAS DISPLACEMENT

RELATED APPLICATIONS

This application claims the benefit of U.S. Provisional Application No. 60/864,113, filed Nov. 2, 2006, entitled VASCULAR ACCESS DEVICE GAS DISPLACEMENT, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes the vascular access device, and allows for intermittent infusion or injection of fluids and pharmaceuticals. An IV access device may include a housing and a septum for closing the system. The septum may be opened with a blunt cannula or a male Luer of a medical device.

When the septum of a vascular access device fails to operate properly, certain complications may occur. Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Current vascular access devices prevent complications, such as infection resulting in CRBSIs, by providing a septum that functions properly during attachment and/or access of the vascular access device by other medical devices. Septa that function properly will act, in part, as infection barriers between the internal and external environments of the vascular access device during attachment and/or access by other medical devices. By functioning properly as infection barriers, septa minimize CRBSI's and other complications.

In order to function properly, a septum needs to open and close during use without difficulty. Often, the gas in a chamber adjacent a septum, must be vented or otherwise displaced as the septum is actuated during use. If neighboring gas chambers are not vented, a septum will be unable to open without significant force. Once opened, the septum will be reluctant to close as a result of neighboring gas chambers that remain compressed under vacuum pressure. Thus, what are needed are various gas chamber venting and displacement structures and methods capable of maximizing proper septum functionality.

BRIEF SUMMARY OF THE INVENTION

The present invention has been developed in response to problems and needs in the art that have not yet been fully resolved by currently available vascular access systems, devices, and methods. Thus, these systems, devices, and methods are developed to provide proper septum functionality by providing gas chamber venting and displacement structures and methods.

A medical device may include a vascular access device that includes a body and a septum at least partially housed within the body, a gas chamber housed between the body and the septum, and a receptacle within the body for receiving gas from the gas chamber as the septum is actuated. The medical device may also include a vent connecting the gas chamber to the receptacle. The receptacle may be a neighboring gas chamber that is near the gas chamber of the device.

The vascular access device may include a cavity below the septum of sufficient volume to receive the receptacle as the receptacle is expanded in volume and to simultaneously permit a separate access device to communicate fluid with the cavity of the device. The septum may also include a bottom disk that is thin enough to cause the bottom disk to balloon and create the receptacle as the septum is actuated and the gas chamber decreases in volume.

The receptacle may be an elastomer in communication with the gas chamber. The elastomer may expand and the receptacle may increase in volume as the gas chamber decreases in volume. The gas chamber may conversely increase in volume as the elastomer contracts and the receptacle decreases in volume.

A method of displacing gas within a medical device may include providing a vascular access device including a body, a septum housed within the body, and a gas chamber between the body and the septum, providing a receptacle within the body, and transferring gas between the gas chamber and the receptacle. Transferring gas between the gas chamber and the receptacle may also include transferring gas through a vent that connects the gas chamber to the receptacle.

The method may also include increasing the total effective volume of the gas chamber by placing the gas chamber in communication with the receptacle, which receptacle may include a volume. Further, if the receptacle includes a volume, the method may also include decreasing the pressure required to compress the gas chamber by placing the gas chamber in communication with the volume of the receptacle, thus increasing the overall combined volume of the receptacle and the gas chamber.

The method may also include ballooning the septum to provide the receptacle. The method may further include providing a cavity capable of receiving the ballooning septum and simultaneously permitting a separate access device to communicate fluid with the cavity. The method may also include expanding the receptacle while decreasing the volume of the gas chamber, and conversely contracting the receptacle while increasing the volume of the gas chamber.

A medical device may include a means for accessing the vascular system of a patient including a body, a septum at least partially housed within the body, and a gas chamber between the body and a portion of the septum. The medical device may also include a means for receiving gas from the gas chamber, and the means for receiving gas from the gas chamber may reside within the means for accessing the vascular system of a patient. The means for receiving gas from the gas chamber may increase the overall effective volume of the gas chamber. The septum may also balloon to create the means for receiving gas from the gas chamber. Further, the means for receiving gas from the gas chamber may be an elastomer in communication with the gas chamber.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
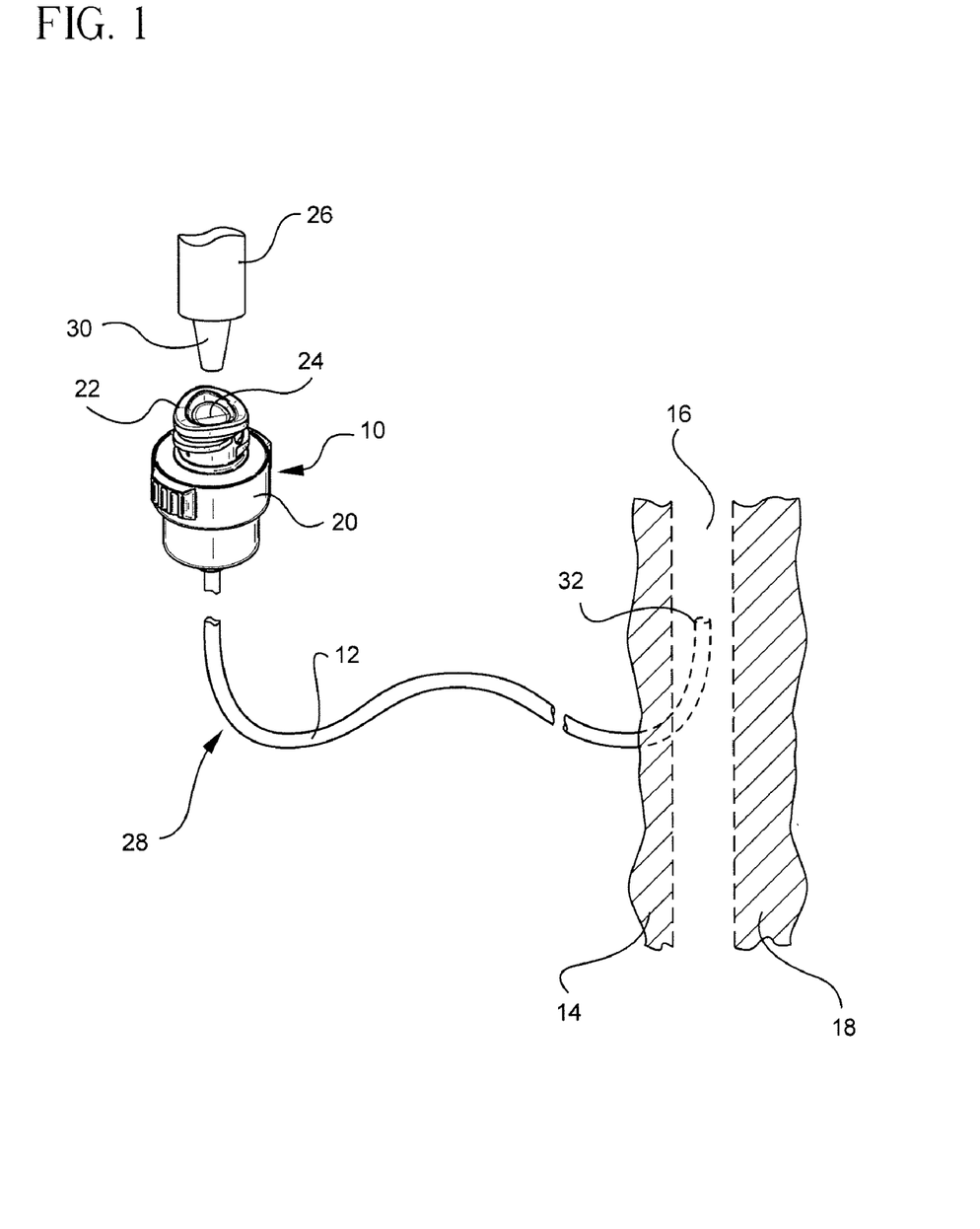
FIG. 1 is a perspective view of an extravascular system connected to the vascular system of a patient.

Referring now to FIG. 1, a vascular access device (also referred to as an extravascular device, intravenous access device, access port, and/or any device attached to or functioning with an extravascular system) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 and all structures used in combination therewith may form a larger extravascular system 28. As part of the system 28, a tip 30 of the separate device 26 may be inserted into the device 10 through the slit 24 of the septum 22. The tip 30 will serve to communicate fluid through the device 10 and the end 32 of the catheter 12 when the device 10 is in use. In an embodiment of the invention, as the tip 30 penetrates the device 10, the two opposing slit 24 surfaces of the septum 22 will separate in opposing lateral directions and will stretch the slit 24 surfaces of the septum 22 in an axial direction, thus increasing the overall height of the septum 22. In this particular embodiment, as the height of the septum is increased, the seal between the device 10 and the tip 30 is rendered more effective.

Figure 2:
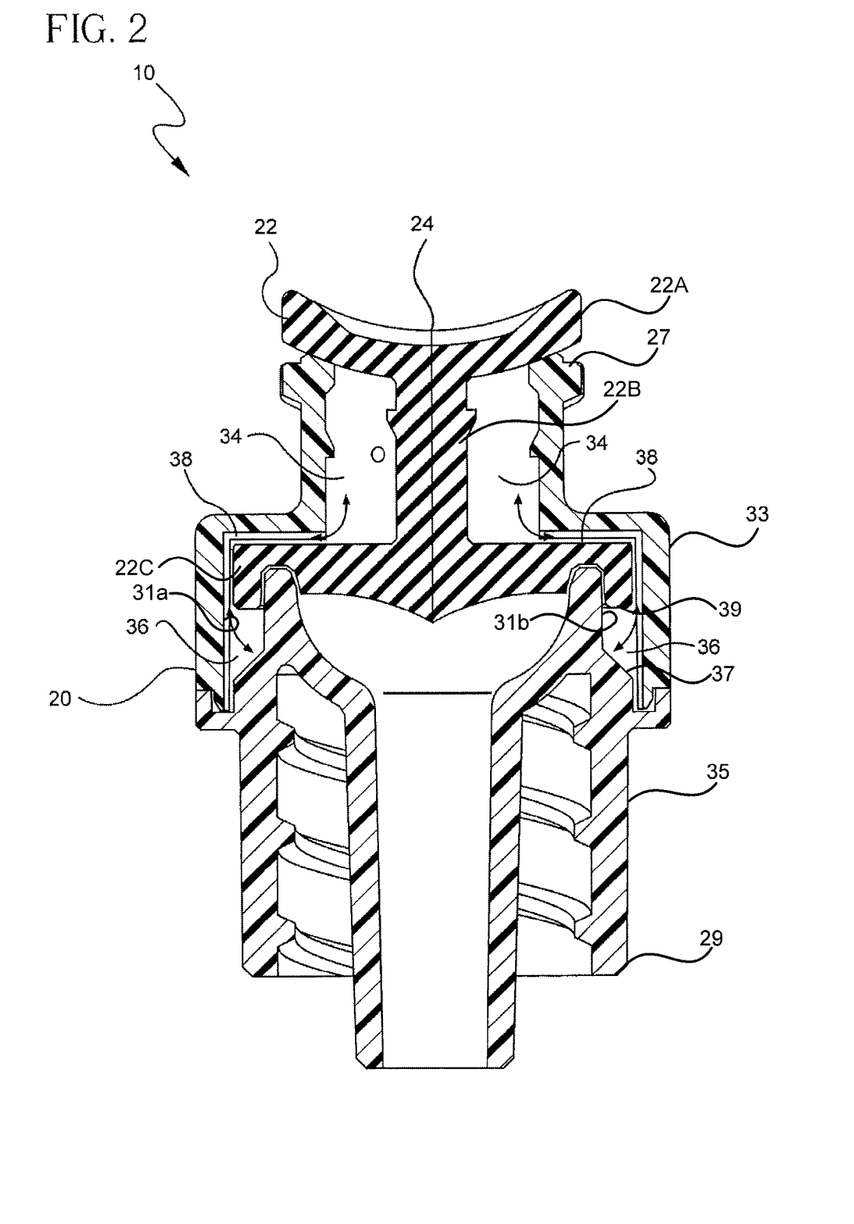
FIG. 2 is a cross section view of a vascular access device with a gas chamber, vent, and receptacle.

Referring now to FIG. 2, a vascular access device 10 includes a body 20, a septum 22 at least partially housed within the body 20, at least one gas chamber 34 housed between the body 20 and the septum 22, and a receptacle 36 within the body 20 for receiving gas from the gas chamber 34 as the septum 22 is actuated. The septum 22 includes a top disc 22A, a bottom disc 22C, and a connecting portion 22B. A vent 38, also housed within the body 20, connects the gas chamber 34 to the receptacle 36. The receptacle 36 may be a neighboring gas chamber that is close in proximity to the gas chamber 34. The purpose of the receptacle 36 is to increase the total effective volume of the gas chamber 34 by placing the gas chamber 34 in communication with the receptacle 36 by means of the vent 38. By increasing the total effective volume of the gas chamber 34, the septum 22 will be able to function properly.

Referring still to FIG. 2, in some embodiments, the body 20 includes a top portion 33 and a bottom portion 35, a proximal end 27 and a distal end 29. In some embodiments, the receptacle 36 is defined on a first side (e.g. the outer radial side 41a) by the top portion 33 of the body 20 and on a second side (e.g. the inner radial side 41a) by the bottom portion of the body 20. In some embodiments, the receptacle 36 is defined on a proximal side 39 by the septum 22, on a distal side 37 by the body, and on a radial side 31a, 31b by the body 20. In some embodiments, the receptacle 36 is defined by the septum 22 on only a proximal side 39. The receptacle 36 can be a neighboring gas chamber to the gas chamber 34.

In traditional vascular access devices that have no vent through the body 20 of the device 10, as the septum 22 is actuated or opened by the insertion of the tip 30 of a separate access device 26, pressure would build within the gas chamber 34 of the device 10. In the current embodiment described with reference to FIG. 2, the increased overall combined volume of the gas chamber 34, the vent 38, and the receptacle 36 provides an increase in overall volume that reduces the percentage of volume that is compressed as the septum 22 is actuated.

Thus, as the tip 30 of a separate access device (not shown in FIG. 2) is inserted into the slit 24 of the septum 22, the volume of the gas chamber 34 decreases, sending gas through the vent 38 and into the receptacle 36. While the total combined volume decreases during septum actuation and access, the percentage of gas within the volume that is compressed is much smaller in relation to the total combined volume than it would otherwise be if the gas chamber 34 was not connected to any other neighboring gas chamber. Thus, in previous vascular access devices without septum vents, the chamber 34 would reach a compression ratio of greater than 90 to 95 percent, causing only 5 to 10 percent of the total volume of the chamber 34 to remain during septum 22 access.

However, under the present embodiment, because the total overall volume of the gas chamber 34, vent 38, and receptacle 36 is much larger than a conventional gas chamber, when the gas chamber 34 is nearly fully compressed, a large amount of volume, i.e., about 40 to 70 percent, remains uncompressed. The volume of the neighboring gas chamber or receptacle 36 may be increased in order to further increase the overall volume and reduce the percentage of volume compressed when the gas chamber 34 is collapsed upon septum 22 access. The receptacle 36 may reside at any point within the device 10, so long as the receptacle 36 is in communication with the gas chamber 34.

By providing a higher level of air pressure within the gas chamber 34, vent 38, and receptacle 36 during use of the device, the septum 22 and other portions of the device 10 may be secured under pressure in order to prevent leakage of fluid within the device or microbial ingress within the device from a surrounding environment.

Figure 3:
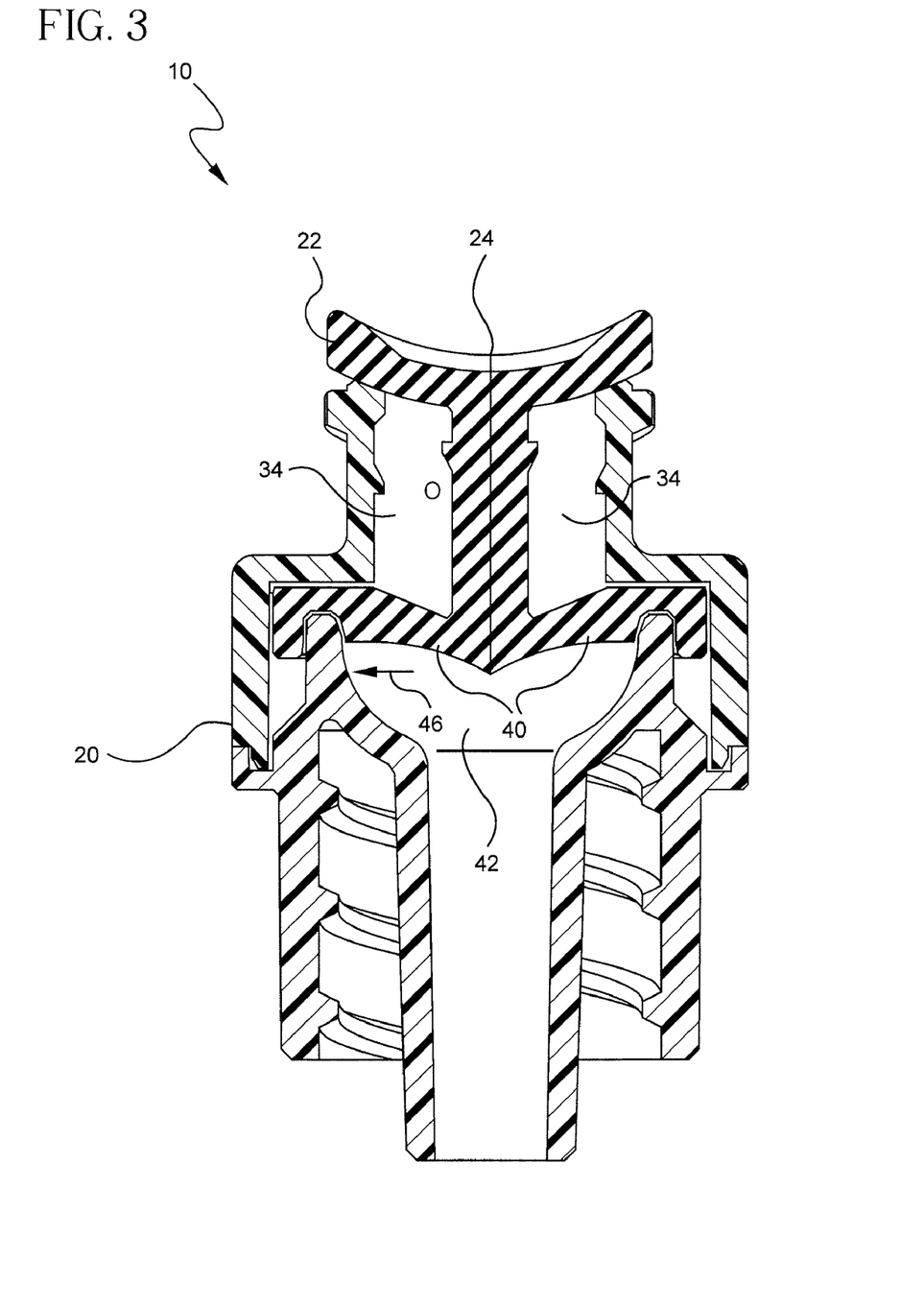
FIG. 3 is a cross section view of a vascular access device with a ballooning septum before insertion of a separate access device.
Figure 4:
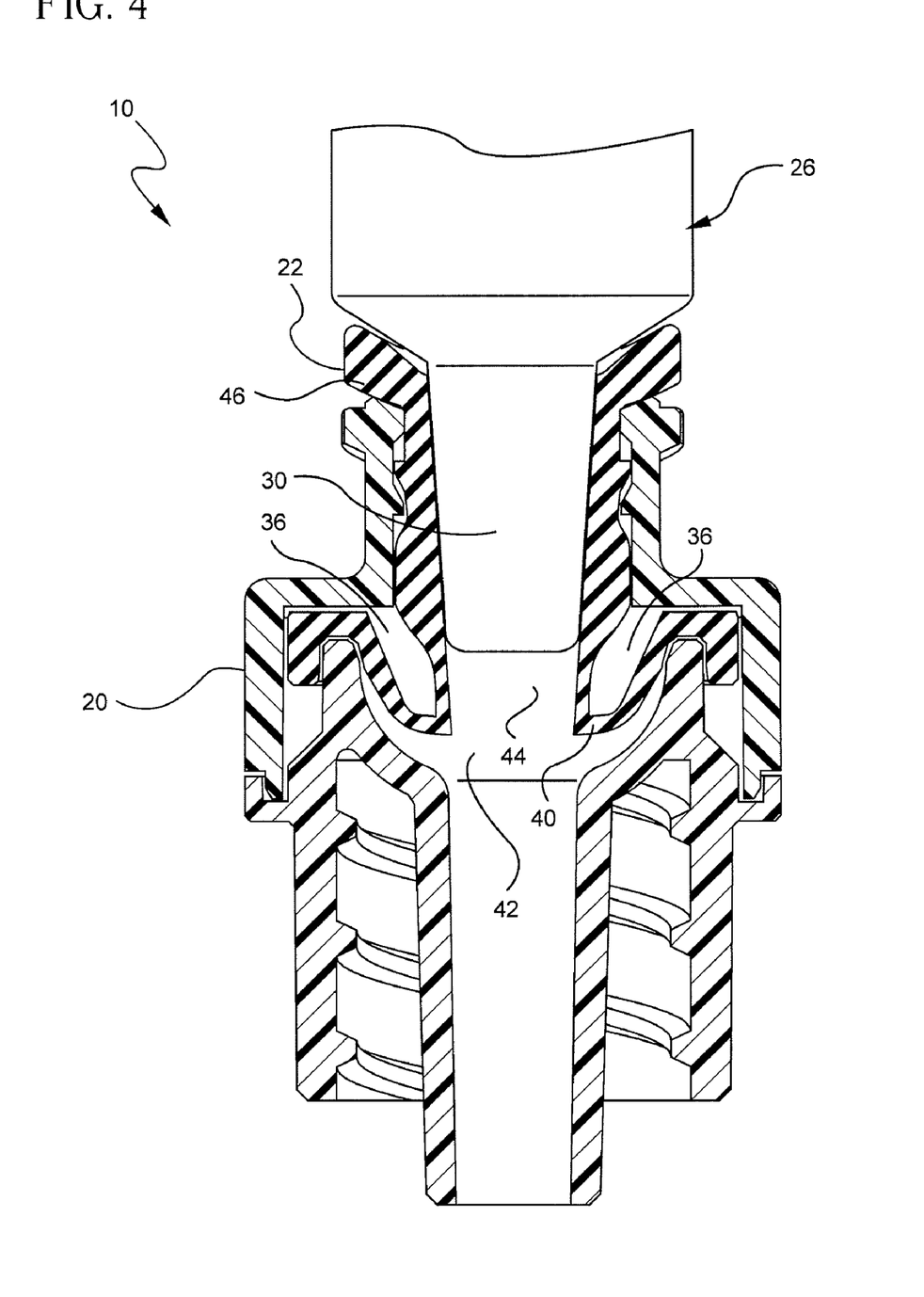
FIG. 4 is a cross section view of a vascular access device with a ballooning septum.

Referring now to FIGS. 3 and 4, a vascular access device 10 includes a body 20 and a septum 22 at least partially housed within the body 20. A gas chamber 34 resides between the septum 22 and the body 20. The septum 22 includes a bottom disk 40 that is thin enough to cause the bottom disk 40 to balloon and create a receptacle 36 as the septum 22 is actuated and the gas chamber 34 decreases in volume upon insertion of the tip 30 of a separate access device 26.

As illustrated in FIG. 3, before the tip 30 is inserted into the device 10, the gas chamber 34 is in full volume. After the tip 30 of a separate access device 26 is inserted into the septum 22, as illustrated in FIG. 4, the volume of the gas chamber 34 is transferred downward into the ballooning portion of the bottom disk 40 of the septum 22. The device 10 includes a cavity 42 below the bottom disk 40 of the septum 22. The cavity 42 is of sufficient volume to receive the receptacle 36 and simultaneously permit the tip 30 of the separate access device 26 to communicate fluid with the cavity through a fluid transfer channel 44.

The bottom disk 40 of the septum 22 is thinned and optimized to allow the bottom disk 40 to balloon into the base and chamber 42 of the device 10. The septum 22 need not necessarily balloon in order for the volume of the gas chamber 34 to be fully transferred into the receptacle 36, so long as the volume of the cavity 42 is large enough to receive the receptacle 36. The volume of the cavity may be increased by either lengthening the cavity 42 or widening the walls of the body 20 surrounding the cavity 42 in a lateral direction 46. The bottom disk 40 of the septum 22 may be thinned or otherwise structured or replaced with a material capable of ballooning to a point at which a user will be able to easily access the septum 22 by inserting the tip 30 of a separate access device 26 with minimal force. However, the ballooning bottom disk 40 should be sufficiently resilient in order to provide the force necessary to return the septum 22 to its original position upon retraction of the tip 30 from the septum 22. Thus, the resiliency of the bottom disk will cause the volume of the receptacle 36 to decrease as the volume of the gas chamber 34 is increased, returning to its original gas chamber 34 position.

Figure 5:
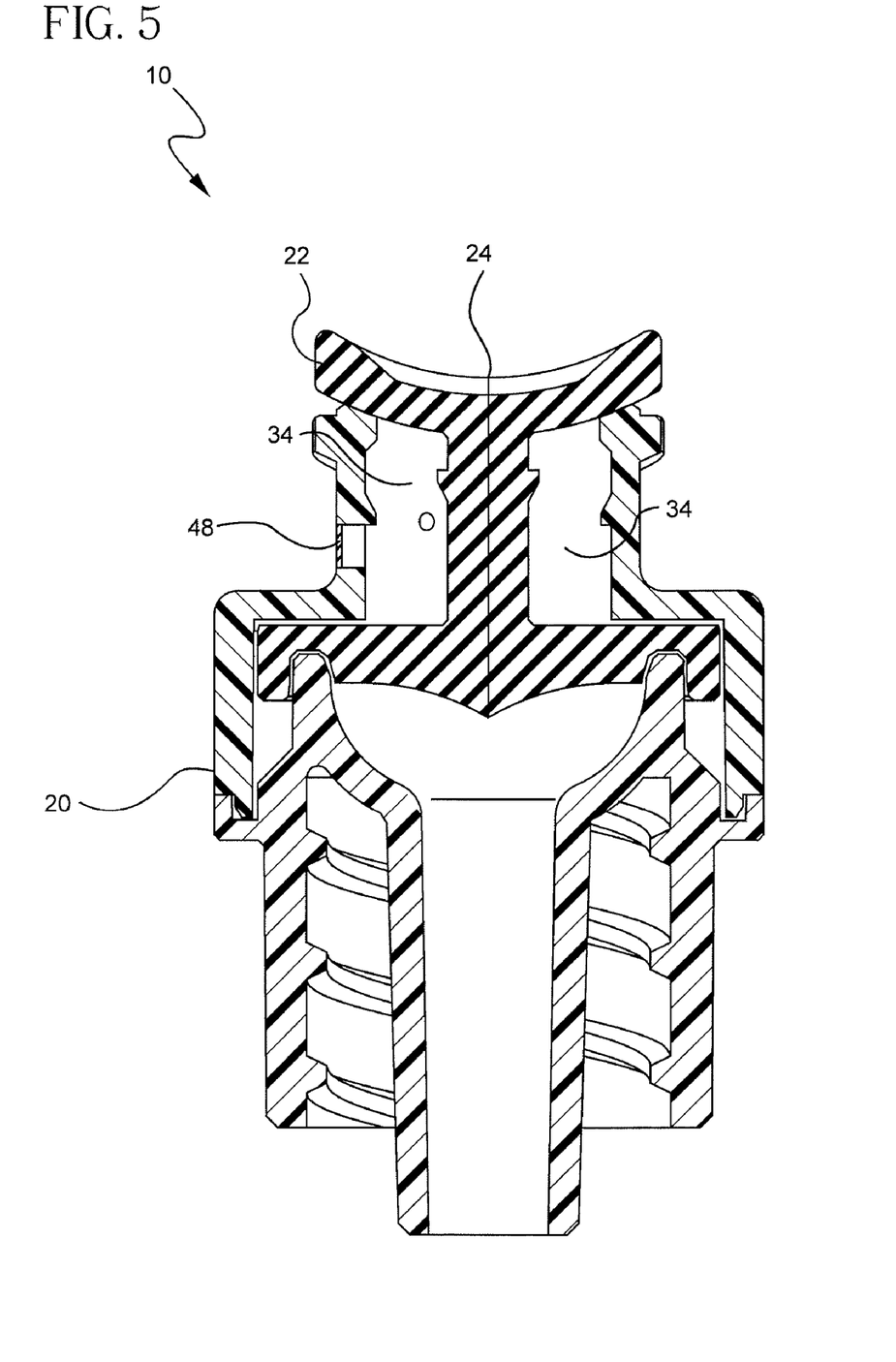
FIG. 5 is a cross section view of a vascular access device with a resting elastomer.
Figure 6:
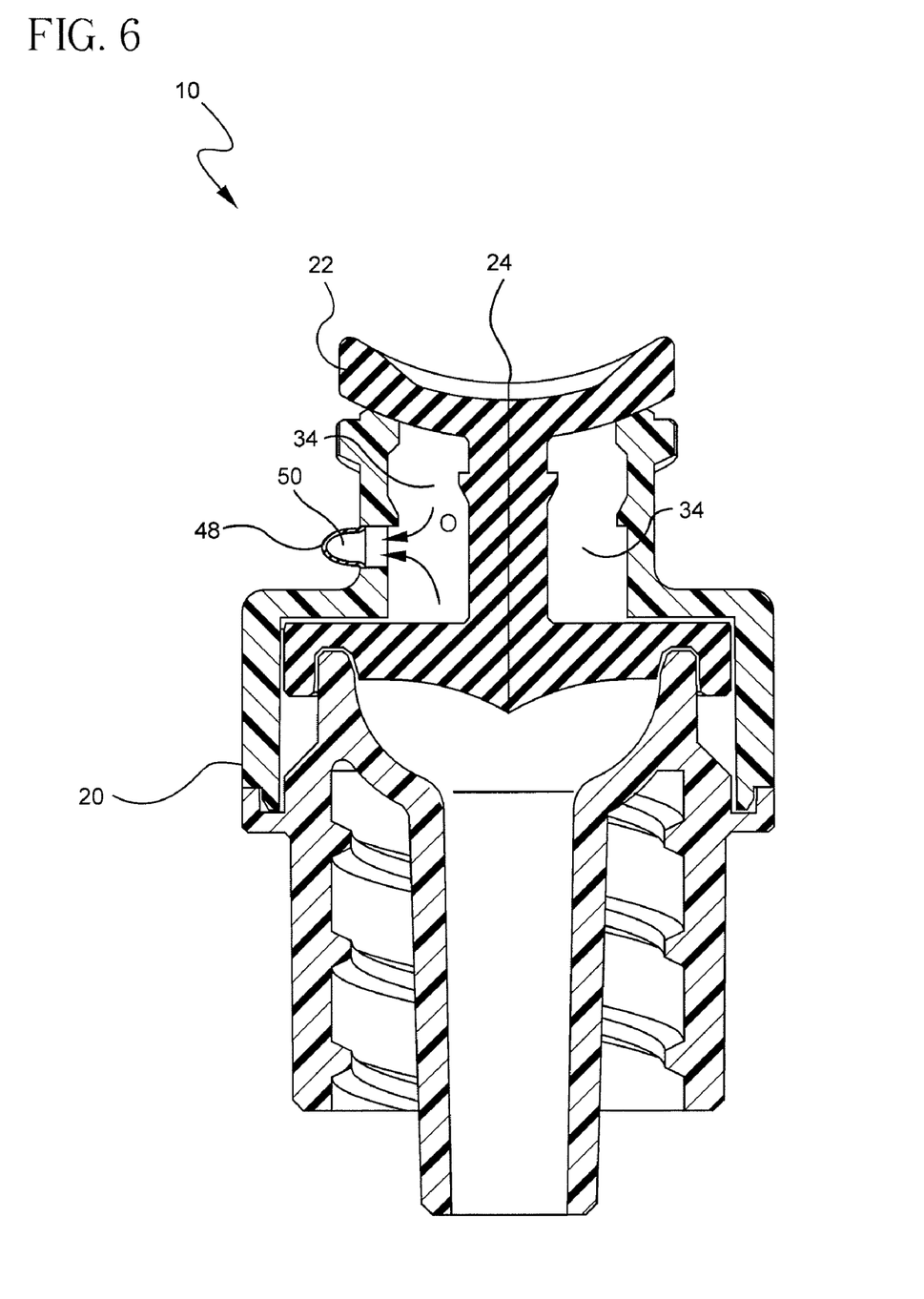
FIG. 6 is a cross section view of the vascular access device of FIG. 4 with the elastomer expanded.

Referring now to FIG. 5, a vascular access device 10 includes a body 20, a septum 22 at least partially housed within the body 20, and at least one gas chamber 34 housed between the septum 22 and the body 20, and an elastomer 48 in communication with the gas chamber 34. In its resting state as shown in FIG. 5, the gas chamber 34 resides at maximum volume and the elastomer 48 is not expanded. FIG. 6 illustrates the functionality of the elastomer 48 upon insertion of the tip 30 of a separate access device 26 into the septum 22.

Referring now to FIG. 6, the vascular access device 10 of FIG. 5 is shown in cross section view with the elastomer 48 expanded, causing an increase in volume within the elastomer. The increase in volume within the elastomer is a receptacle 50 for receiving gas from the gas chamber 34. The elastomer 48 expands and the receptacle 50 increases in volume as the gas chamber 34 decreases in volume. Conversely, as the tip 30 of a separate access device 26 is removed from the septum 22, the resilient nature of the elastomer 48 causes the elastomer 48 to contract, consequently causing the gas chamber 34 to increase in volume as the receptacle 50 decreases in volume and the elastomer 48 returns to its original resting position as shown in FIG. 5. Thus, during insertion of a separate access device 26 into the septum 22, or during any other actuation of the septum 22, air may be displaced or otherwise transferred from the gas chamber 34 into a receptacle 50 that is in communication with the gas chamber 34.

Figure 6A:
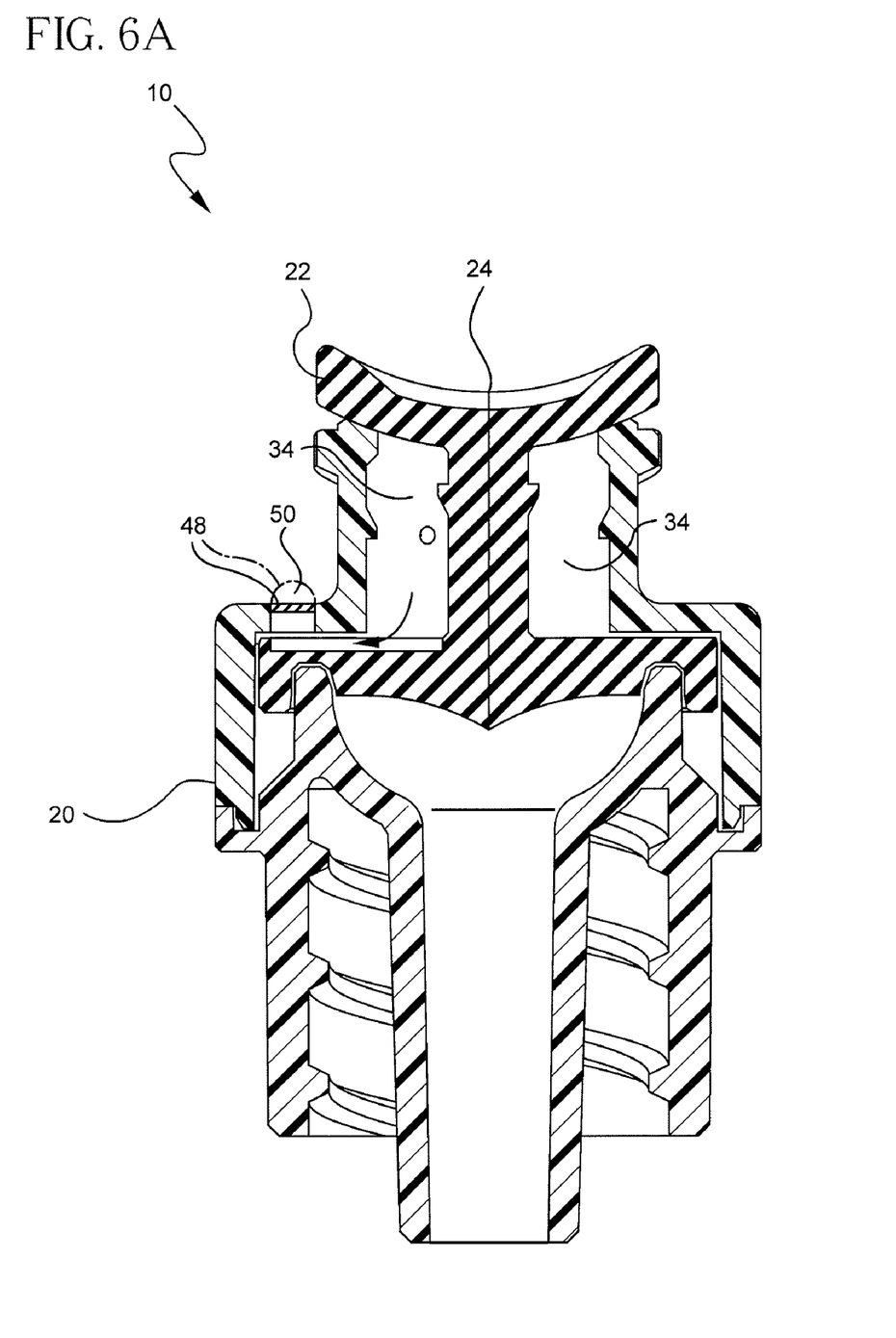
FIG. 6A is a partial cross section view of a vascular access device with an elastomer in an alternate location.

The elastomer 48 and receptacle 50 may be located at any functional or non-functional area of the device 10. For example, the elastomer may be placed upon the shoulder of the body 20 as shown in FIG. 6A.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A vascular access device, comprising:
    a body;
    a unitary septum at least partially housed within the body, the septum having a top disc and bottom disc and a slit extending through the top and the bottom discs, a portion of the top disc remaining fixedly positioned on the body when the unitary septum is in an open and a closed position;
    a gas chamber defined between the body and the top and bottom discs of the unitary septum;
    a neighboring gas chamber within the body, the neighboring gas chamber being defined on a proximal side by the septum and on a distal side and a radial side by the body; and
    a vent connecting the gas chamber and the neighboring gas chamber.

2. The vascular access device of claim 1, wherein the body includes a cavity below the septum of sufficient volume to permit a separate access device to communicate fluid with the cavity.

3. The medical device of claim 1, wherein the neighboring gas chamber is an elastomer in communication with the gas chamber.

4. The medical device of claim 1, wherein the septum further includes a connecting portion connecting the top and bottom discs, and a slit extending through the top and bottom discs and the connecting portion.

5. The medical device of claim 4, wherein the gas chamber is between the top disc of the septum, the bottom disc of the septum, the connecting portion of the septum, and an interior surface of the body.

6. The vascular access device of claim 1, wherein the vent is disposed between the body and the bottom disc.

7. A medical device, comprising:
- a body having a top portion and a bottom portion;
- a septum at least partially housed within the body, the septum having a top disc and a bottom disc, a portion of the top disc remaining fixedly positioned on the body when the unitary septum is in an open and a closed position;
- a gas chamber defined between the body and the top and bottom discs of the septum;
- a neighboring gas chamber coupled to the body, the neighboring gas chamber being defined on a first side by the top portion of the body and on a second side by the bottom portion of the body;
- a vent placing the gas chamber in gaseous communication with the neighboring gas chamber.

8. The medical device of claim 7, wherein the neighboring gas chamber increases the overall effective volume of the gas chamber.

9. The vascular access device of claim 7, wherein the vent is disposed between the body and the bottom disc.

10. A vascular access device, comprising:
- a body;
- a unitary septum at least partially housed within the body, the septum having a top portion, a bottom portion, and a slit extending through the top and the bottom portions, the top portions remaining fixedly positioned on the body when the unitary septum is in an open and a closed position;
- a gas chamber between the body and the top and bottom portions of the unitary septum;
- a neighboring gas chamber within the body, the neighboring gas chamber being defined by the septum on only a proximal side; and
- a vent defined between the body and a portion of the septum, the vent connecting the gas chamber and the neighboring gas chamber.

11. The vascular access device of claim 10, wherein the vent is disposed between the body and the bottom portion of the unitary septum.

\* \* \* \* \*